United States Patent [19]

Saitoh et al.

[11] Patent Number: 6,030,795
[45] Date of Patent: Feb. 29, 2000

[54] RECOMBINANT TGF-β TYPE I RECEPTOR VARIANTS HAVING DIFFERENTIALLY DIMINISHED CAPACITY TO SIGNAL FOR MATRIX PROTEIN PRODUCTION

[75] Inventors: Masae Saitoh; Kohei Miyazono; Hidenori Ichijo, all of Tokyo, Japan

[73] Assignee: Ludwig Institute for Cancer Research, New York, N.Y.

[21] Appl. No.: 09/029,424

[22] PCT Filed: Sep. 4, 1996

[86] PCT No.: PCT/GB96/02179

§ 371 Date: Apr. 28, 1998

§ 102(e) Date: Apr. 28, 1998

[87] PCT Pub. No.: WO97/11173

PCT Pub. Date: Mar. 27, 1997

[30] Foreign Application Priority Data

Sep. 4, 1995 [GB] United Kingdom .................. 9517992

[51] Int. Cl.$^7$ ............................ C12N 15/12; C07K 14/71; G01N 33/53
[52] U.S. Cl. .................... 435/7.21; 435/325; 435/252.3; 435/320.1; 536/23.5; 530/350; 514/2
[58] Field of Search ........................ 536/23.5; 435/320.1, 435/325, 252.3, 7.21; 530/350; 514/2

[56] References Cited

PUBLICATIONS

Chen et al., J. Biol. Chem. 270: 12235–41, 1995.
Armes et al., J. Biol. Chem. 274: 7929–35, 1999.
Miettinen et al., J. Cell, Biol. 127:2021–2036, 1994.
Franzén et al., Biochem. Biophys. Res. Commun. 207:682–689, 1995.
Feng et al., J. Biol. Chem. 270:24237–24245, 1995.
Weiser et al., EMBO J. 14:2199–2208, 1995.
Franén et al., Cell 75:681–692, 1993.
Saitoh et al., J. Biol. Chem. 271:2769–2775, 1996.
Souchelnytskyi et al., EMBO J. 15:6231–6240, 1996.

Primary Examiner—David L. Fitzgerald
Attorney, Agent, or Firm—Wolf, Greenfield & Sacks, P.C.

[57] ABSTRACT

The invention provides modified mammalian transforming growth factor (TGF)-β type I receptors (TβR-I) which substantially retain the ability of native TβR-I to transduce signals for matrix protein production but which have a diminished capacity to transduce growth-inhibitory signals. The receptors of the invention are characterized by the replacement or deletion of one or more residues in the juxtamembrane region between the transmembrane and GS domains, e.g., the residues corresponding to Ser$^{172}$ or Thr$^{176}$ of hTβR-I. The invention also provides recombinant expression systems for production of the modified receptors and assays using them for the identification of antiproliferative agents.

20 Claims, 3 Drawing Sheets

RECOMBINANT TGF-β TYPE I RECEPTOR VARIANTS HAVING DIFFERENTIALLY DIMINISHED CAPACITY TO SIGNAL FOR MATRIX PROTEIN PRODUCTION

This application is a national stage application under 35 U.S.C. §371 of PCT/GB96/02179, filed Sep. 4, 1996, which claims priority to Great Britain application no. 9517992.5, filed Sep. 4, 1995.

1. Field of the Invention

This invention relates to a nucleic acid molecule encoding a type I receptor of the TGF-β superfamily having modified growth inhibition, and its use.

2. Background of the Invention

Cell growth and differentiation in a multicellular organism are critically regulated by members of transforming growth factor-β (TGF-β) superfamily including TGF-β, activin/inhibin, bone morphogenetic protein (BMP), Mullerian-inhibiting substance and glial cell line-derived neurotrophic factor. TGF-β is a prototype in this superfamily of structurally related molecules, and regulates cell proliferation, extracellular matrix formation, migration, adhesion and many other cellular functions important for development and homeostasis.

Certain members of the TGF-β superfamily exert their biological actions through heteromeric complexes of two types (type I and type II) of transmembrane receptors with a serine/threonine kinase domain in their cytoplasmic region. Six different type I receptors have been identified in mammals (ten Dijke et al (1994) Prog. Growth Factor Res. 5:55–72), including one TGF-β type I receptor (TβR-I), two activin type I receptors (ActR-I and ActR-IB), two BMP type I receptors (BMPR-IA and BMPR-IB) and one additional type I receptor called ALK-1. The type I receptors have similar sizes (502–532 amino acid residues) and 60–90% amino acid sequence identities to each other in their kinase domains. In addition, type I receptors contain a conserved sequence known as the GS domain (also called type I box) in their cytoplasmic juxtamembrane region (Attisano et al (1994) Biochem. Biophys. Acta 1222:71–80). Type I receptors are more similar to each other than they are to the known type II receptors including TGF-β type II receptor (TβR-II) and two activin type II receptors (ActR-II and ActR-IIB), and thus form a subgroup of mammalian type I receptors in the family of receptor serine/threonine kinases.

Studies on transmembrane serine/threonine kinases have disclosed that certain members of TGF-β superfamily exert their multiple effects through binding to unique sets of heteromeric complexes between type I and type II receptors. In the case of TGF-β, TβR-II is a constitutively active kinase and capable of binding TGF-β in the absence of TβR-I, whereas TβR-I requires TβR-II for the ligand-binding. The TβR-I kinase appears to be activated by formation of a hetero-oligomeric complex composed of TGF-β, TβR-II and TβR-I. In the complex, several serine and threonine residues in the GS domain of TBR-I become phosphorylated by TβR-II, and the phosphorylation of GS domain is essential for TGF-β signalling; however, the functional role of phosphorylated serine and threonine residues in the GS domain as well as the mechanism of signalling after the phosphorylation are largely unknown. In addition, the functional importance of the TβR-I cytoplasmic region other than the GS domain has yet to be elucidated.

Mutational analyses altering serine and threonine residues in the TβR-I GS domain have revealed that phosphorylation of certain serines and threonines by TβR-II is essential for TGF-β signalling although its signalling activity does not appear to depend on the phosphorylation of any particular serine or threonine residue in the TTSGSGSG sequence SEQ ID NO:19 of the GS domain (Wieser et al (1995) Embo. J. 14:2199–2208). In addition, recent identification of a constitutively active form of TβR-I which does not require TβR-II and TGF-β for signalling suggested that TβR-I acts as a downstream signalling molecule of TβR-II (Wieser et al (1995) supra).

Despite the functional importance of the GS domain for initiating intracellular signals, little is known about how the signals are propagated after phosphorylation of the GS domain. Based on the knowledge of receptor tyrosine kinases, one possible mechanism could be that the phosphorylated serine and/or threonine residues in the GS domain may act as the binding sites for the intracellular substrate to be activated by the TβR-I kinase. This hypothesis is attractive to explain the signalling mechanism for certain common effects induced by the members of TGF-β superfamily since the GS domain of the known type I receptors is highly conserved. On the other hand, amino acid sequences of the GS domain of the type I receptors might be too similar to each other to confer specificities to the signals which mediate a wide variety of responses induced by the TGFβ superfamily. In fact, a TβR-I chimeric receptor substituting ActR-I GS domain for TβR-I GS domain still has the TGF-β-induced antiproliferative signal which is not mediated through intact ActR-I (Wieser et al (1995) supra). Thus, certain region(s) other than the GS domain in the type I receptors may also be important for diverse signalling activities of the TGF-β superfamily.

Both growth inhibition and matrix formation by TGF-β are potent, and physiologically important. However, these effects are not always desirable during the process of human diseases. For example, cancer cells grow autonomously, and therefore the growth inhibitory effect of TGF-β is important. Matrix formation induced by TGF-β is undesirable, because it induces fibrosis of the tissues, which is found in certain cancer tissues, i.e. gastric cancer and hepatoma. Thus, matrix formation by TGF-β is preferably inhibited, in the treatment of cancer, while keeping the growth inhibitory activity of TGF-β intact.

SUMMARY OF THE INVENTION

According to this invention, novel TGF receptors are mutated such that they substantially retain their matrix formation effect, and exhibit reduced (e.g. to a level no more than 50%, preferably no more than 25%) growth inhibitory effect. The invention relates also to any fragment of such materials which retain these characteristics, and corresponding nucleotides.

The new TβR-I mutants are useful to identify intracellular substrates which transduce the growth inhibitory signal but not the matrix formation signal. The mutants are also useful for screening drugs that can be used for these purposes. The mutants are also of utility in making transgenic mammals such as mice, the consequence of which may be important to understand the growth inhibitory activity and matrix formation activity in vivo, by comparison with wild-type TβR-I and kinase-deficient mutants.

More specifically, we have investigated the role of cytoplasmic juxtamembrane region located between the transmembrane domain and the GS domain of TβR-I by mutational analyses using mutant mink lung epithelial cells which lack endogenous TβR-I. Upon transfection, wild-type TβR-I restored the TGF-β signals for growth inhibition and induction of plasminogen activator inhibitor (PAI)-1 and fibronectin. A deletion mutant, TβR-I/JD1(Δ150-181), which lacks the juxtamembrane region preceding the GS domain, bound TGF-β in concert with TβR-II and transduced a signal leading to induction of PAI-1 and fibronectin but not growth inhibition. Recombinant receptors with mutations that change serine 172 to alanine (S172A) or threonine 176 to valine (T176V) were similar to wild-type TβR-I in their abilities to bind TGF-β, formed complexes with TβR-II, and transduced a signal for PAI1 and fibronectin. Similarly to TβR-I/JD1(Δ150-181), however, these missense mutant receptors were impaired in their effect to mediate a growth inhibitory signal. These observations indicate that serine 172 and threonine 176 of TβR-I are dispensable for extracellular matrix protein production but essential to the growth inhibition by TGF-β.

DESCRIPTION OF THE INVENTION

Figure 1:
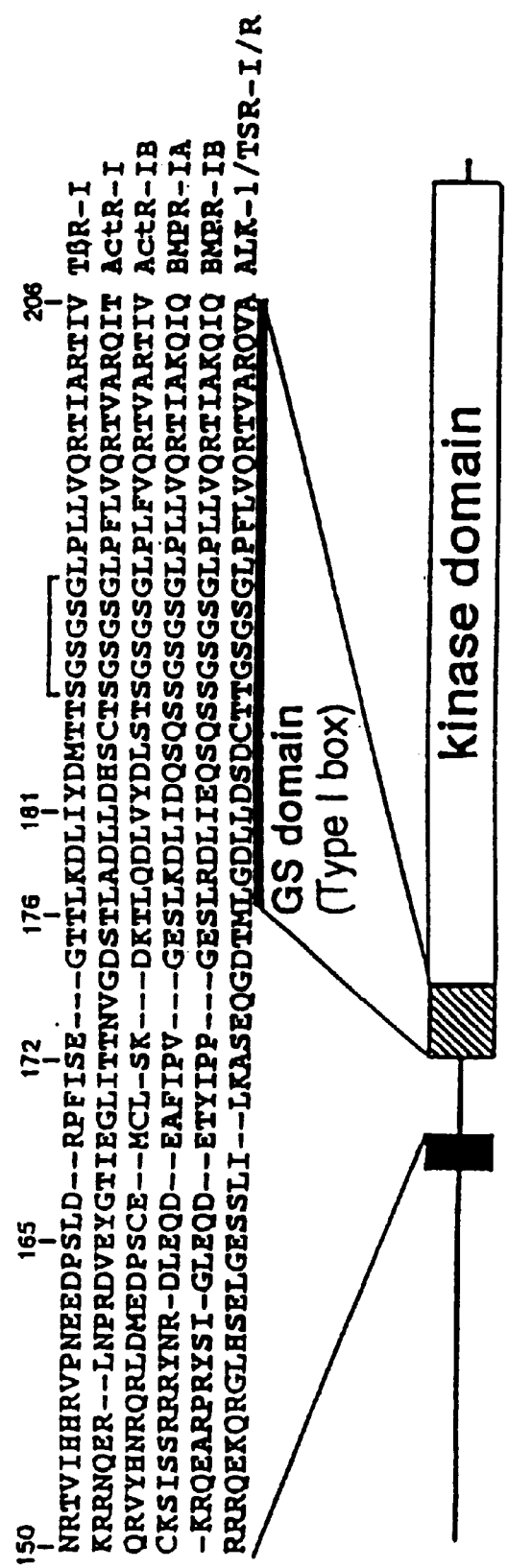
FIG. 1 shows the sequence alignment of the cytoplasmic juxtamembrane region of different type I receptors (ten Dijke et al (1994) Prog. Growth Factor Res. 5:55–72). The sequence identifiers of the receptor fragments are as follows: TβR-I is SEQ ID NO: 13; ActR-I is SEQ ID NO: 14; ActR-IB is SEQ ID NO: 15; BMPR-IA is SEQ ID NO: 16; BMPR-IB is SEQ ID NO: 17; and ALK-I/TSR-I/R is SEQ ID NO: 18.

The following abbreviations are used herein:

TGFβ, transforming growth factor-β; BMP, bone morphogenetic protein; TβR, TGF-β receptor; ActRI, activin receptor; BMPR, BMP receptor; ALK, activin receptor-like kinase; PAI, plasminogen activator inhibitor; PCR, polymerase chain reaction; GST, glutathione S-transferase; DMEM, Dulbecco's modified Eagle's medium; FBS, fetal bovine serum; PBS, phosphate buffered saline; DSS, disuccinimidyl suberate; SDS, sodium dodecyl sulfate; DTT, dithiothreitol; IPTG, isopropylthiogalactopyranoside.

Various oligonucleotides (see also the Sequence Listing; SEQ ID Nos. 1–12) were used to generate expression constructs. The sequences of the oligonucleotide primers are presented below in the 5' to 3' direction. Numbering is based on the nucleotide sequence of TβR-I (Franzen et al (1993) Cell 75:681–692). Restriction enzyme sites incorporated into the primers are underlined. The junction of the deletion primer RISdel5 is indicated by a.

RIS1-sma: GT<u>CCCGGG</u>CTGCCACAACCGCACT (nucleotides; 441–445 SEQ ID NO:1)
RISdel2-sma: GC<u>CCCGGG</u>TTATGATATGACA (nucleotides; 544–555 SEQ ID NO:2)
RIS0-hind: GG<u>AAGCTT</u>GACCATGGAGGCG (nucleotides; 1–13 SEQ ID NO:3)
RIAS-not: AG<u>GCGGCCGC</u>TTACATTTTGATGCC (nucleotides; 1512–1498 SEQ ID NO:4)
RIASdel1: GTGGCAGATATAGACCATCAAC (nucleotides; 446–425 SEQ ID NO:5)
RISdel5: CTATATCTGCCAC-TATGATATGACA (nucleotides; 433–445, 544–555 SEQ ID NO:6)
S-1: CCTGCATTAGATCGCCCTTTTAT (nucleotides; 492–514 SEQ ID NO:7)
S-2: CGCCCTTTTATTGCAGAGGGTACT (nucleotides; 504–527 SEQ ID NO:8)
S-3: GAGGGTACTGTGTTGAAAGAC (nucleotides; 519–539 SEQ ID NO:9)
AS-1: ATAAAAGGGCGATCTAATGCAGG (nucleotides; 514–492 SEQ ID NO:10)
AS-2: AGTACCCTCTGCAATAAAAGGGCG (nucleotides; 527–504 SEQ ID NO:11)
AS-3: GTCTTTCAACACAGTACCCTC (nucleotides; 539–519 SEQ ID NO:12)

cDNA Constructions—Stable expression vectors of wild-type TβR-I and its mutant derivatives were prepared by subcloning PCR-generated cDNA fragments into pMEP4 vector, a $Zn^{2+}$-inducible mammalian expression vector (Wrana et al (1992) Cell 71:1003–1014). To construct wild-type TβR-I-pMEP4, primer RIS0-hind and primer RIAS-not were used to amplify the coding region of TβR-I cDNA. Reaction conditions were 1 min at 94° C., 1 min at 48° C., and 2 min at 72° C. for 30 cycles. The PCR products were digested with HindIII and NotI, and subcloned into the pMEP4 vector. To construct the deletion mutant TβR-I/JD1 (Δ150-181), the primers RIS0-hind and RIASdel1 were used to amplify the 5' part of TβR-I cDNA fragment, and the primers RISdel5 and RIAS-not were used for the 3' fragment. The two primary PCR products were gel-purified, mixed and subjected to reamplification with primers RIS0-hind and RIAS-not. The secondary PCR products were digested with HindIII and NotI, and subcloned into the pMEP4 vector. Likewise, for the constructions of single missense mutants TβR-I/JM1(S165A), TβR-I/JM2(S172A) and TβR-I/JM3 (T176V), primer RIS0-hind and the mutant antisense primer (AS-1, AS-2 and AS-3, respectively) were used to amplify the 5' fragments, and the mutant sense primer (S-1, S-2 and S-3, respectively) and primer RIAS-not were used to amplify the 3' fragments. PCR products were mixed in respective combinations, and reamplified with primers RIS0-hind and RIAS-not. For TβR-I/JM123 (S165A/S172A/T176V), PCR was performed using TβR-I/JM1 as a template for the 5' fragment with primers RIS0-hind and AS-2, and TβR-I/JM3 as a template for the 3' fragment with primers S-2 and RIAS-not. The two PCR fragments were mixed and reamplified with primers RIS0-hind and RIAS-not. The SmaI-XbaI fragments of the mutant PCR products were swapped for the corresponding region of wild-type TβR-I plasmid.

Expression vectors for bacterial expression of wild-type TβR-I glutathione S-transferase (GST) fusion proteins (GST-WT) its deletion mutant GST-JD1(Δ150-181) and missense mutants GST-JM1(S165A), GSTJM2(S172A), GST-JM3(T176V) and GST-JM1 23(S165A/S172A/T176V), were obtained by insertion of PCR-generated fragments of the corresponding cytoplasmic regions of TβR-I into pGEX-4T-1 (Pharmacia) using their stable expression plasmids as templates with RIS1-sma or RISdel2-sma as sense primers and RIAS-not as an antisense primer. PCR conditions were 1 min at 94° C., 1 min at 54° C., and 1 min at 72° C. for 25 cycles. The resulting PCR products for the GST fusion protein constructs were digested with SmaI and NotI, and ligated in-frame into pGEX-4T-1.

The structures of PCR-amplified region of the recombinants were all confirmed by sequencing using a Sequenase DNA sequencing kit (U.S. Biochemical). Cell Culture and Transfection—The Mv1Lu mink lung epithelial cells (CCL-64; American Type Culture Collection) and the R mutant Mv1Lu cells (clone 4-2; R4-2) (Laiho et al (1990) J. Biol. Chem. 265:18518–18524) were maintained in DMEM (Nissui) supplemented with 10% FBS and 100 units/ml penicillin. To generate stable transfectants expressing the various mutant forms of TβR-I, R4-2 cells were transfected by the calcium phosphate precipitation method using Eukaryotic transfection kit (Promega). Selection of transfected cells was performed in the presence of 120 U/ml of hygromycin B (Wako Chemicals). Resistant cell colonies were examined for the expression of TβR-I and its mutants by the receptor affinity-labelling assays using $^{125}$ITGF-β1 after induction of the recombinant proteins by $ZnCl_2$. More than two independent clones for each of the transfectants were subjected to the following experiments.

Receptor Binding Assay of TβR-1 Mutants—Recombinant human TGF-β1 (Kirin Brewery Company) was iodinated using the chloramine T method as described in Frolik et al (1984) J. Biol. Chem. 259:10995–1100. Affinity cross-linking experiments were performed with cells pretreated in DMEM containing 0.2% FBS with or without 100 μM $ZnCl_2$ for 6 h, followed by the binding of $^{125}$I-TGF-β1 in PBS containing 0.1% bovine serum albumin for 3 h at 4° C. After washing the cells with PBS three times, the ligand-receptor complexes were cross-linked with 0.27 mM DSS (Pierce Chemical Co.). Cells were washed once with 10 mM Tris-HCl (pH 7.4) containing 1 mM EDTA and 10% glycerol, and solubilized by incubation in TNE buffer (10 mM Tris-HCl, pH 7.5, 150 mM NaCl, 1 mM EDTA, 1% NP-40) containing 1.5% of aprotinin for 20 min at 4° C. For immunoprecipitation of the cross-linked complexes, cell lysates were then incubated with an antiserum against TβR-II (Franzen et al (1993) Cell 75:681–692) for 60 min at 4° C. Immune complexes were bound to protein A-Sepharose (Kabi Pharmacia) for 45 min at 4° C., washed once with TNE buffer, and eluted by boiling in SDS-sample buffer (100 mM Tris, pH 8.8, 0.01% bromophenol blue, 36% glycerol, 4% SDS) in the presence of 10 mM dithiothreitol (DTT). The samples were analyzed by SDS-8.5% polyacrylamide gel electrophoresis and Fuji BAS 2000 Bio-Imaging Analyzer (Fuji Photo Film).

Cell Proliferation Assay—Cells were plated into 24-well plates at $5 \times 10^4$ cells per well in DMEM containing 10% FBS, grown overnight and placed in DMEM containing 0.2% FBS in the presence or absence of 100 μM $ZnCl_2$ for 5 h. The cells were then added with TGF-β1, incubated for additional 16 h, and pulsed with 1 μCi/ml of [$^3$H]thymidine (6.7 Ci/mmol, Amersham) for 2 h. They were fixed on ice with 12.5% trichloroacetic acid, lysed with 1 N NaOH, and the [$^3$H]thymidine incorporation into the DNA was determined by a liquid scintillation counter.

PAI-1 Assay—PAI-1 assays were performed as previously described with minor modifications (Carcamo et al (1994) Mol. Cell. Biol. 14:3810–3821). Briefly, subconfluent cells in 6-well plates were incubated for 5 h with DMEM containing 0.2% FBS and 100 μM $ZnCl_2$. Cells were washed once with PBS and incubated for 4 h in methionine- and cysteine-free DMEM (ICN Biomedicals Inc.) containing 100 μM $ZnCl_2$ with or without 50 ng/ml of TGF-β1. During the final 2 h of incubation, 30 μCi of [$^{35}$S]methionine and [$^{35}$S]cysteine mixture (Pro-mix cell labelling mix; Amersham) was added to the cells. The cells were then removed by washing once in PBS, four times in 10 mM Tris-HCl, pH 8.0, 0.5% sodium deoxycholate, 1 mM phenylmethylsulfonyl fluoride, two times in 2 mM Tris-HCl, pH 8.0, and once in PBS. Proteins were extracted from plastics by SDS-sample buffer containing 10 mM DTT and were analyzed by SDS-10% polyacrylamide gel electrophoresis and Bio-Imaging Analyzer.

Fibronectin Assay—Measurement of fibronectin was performed as described with minor modifications (Wrana et al (1992) supra). Cells grown overnight in 6-well plates were incubated for 5 h with DMEM containing 0.2% FBS and 100 μM $ZnCl_2$. The cells were then added with or without 50 ng/ml of TGF-β1, incubated for 20 h and labelled with 50 μCi/ml of [$^{35}$S]methionine and [$^{35}$S]cysteine mixture in methionine- and cysteine-free DMEM for the final 4 h. The labelled culture media were incubated overnight with 100 μl of gelatin-Sepharose (Pharmacia) in the presence of 0.5% Triton X-100. The beads were washed once in Tris-buffered saline (50 mM Tris-HCl, pH 7.4, 150 mM NaCl), once in 50 mM Tris-HCl (pH 7.4), 0.5 M NaCl, and once in Tris-buffered saline. The fibronectin was eluted by boiling in SDS-sample buffer in the presence of 10 mM DTT. The samples were analyzed by SDS-7% polyacrylamide gel electrophoresis and Bio-Imaging Analyzer.

GST Fusion Proteins—The GST fusion protein constructs were transformed into JM109 bacteria. Overnight cultures were diluted 1:8 in fresh medium and after shaking for 2 h, isopropylthiogalactopyranoside (IPTG, 0.5 mM final concentration) was added. After another 3 h shaking at 30° C., the cells were lysed in PBS containing 1% Triton X-100, 1% Tween-20, 1% sodium deoxycholate and 1 mM DTT, sonicated for 1 min, and centrifuged for 5 min. The supernatants were incubated with glutathione-Sepharose beads (glutathione-Sepharose 4B; Pharmacia) (5:1 vol/vol) for 1 h at 4° C. After extensive washing in PBS, the beads were subjected to phosphorylation assays.

Protein Kinase Assay—25 μl glutathione-Sepharose beads which attached GST fusion proteins were washed once with kinase buffer (20 mM Hepes, pH 7.4, 100 mM NaCl, 10 mM $MnCl_2$, 0.5 mM DTT, 0.05% Triton X100). 25 μl kinase buffer containing 1 μCi of [γ-$^{32}$P]ATP (Amersham) was added. The beads were incubated for 15 min at 4° C. Proteins were resolved on SDS-10% polyacrylamide gel under reducing conditions and analyzed by Bio-Imaging Analyzer.

The following illustrates products of the invention and their utility.

32 amino acids of TβR-I in the juxtamembrane region were deleted, yielding TβR-I/JD1(Δ150-181). The wild-type TβR-I and mutant TβR-I/JD1(Δ150-181) in pMEP4, a $Zn^{2+}$-inducible vector, were stably transfected into a TβR-I-defective Mv1Lu cell line, (R4-2). The expression of the exogenous receptors and their complex formation with the endogenous TβR-II were tested by affinity cross-linking of the cells using $^{125}$ITGF-β1 followed by immunoprecipitating the ligand-receptor complexes with anti-TβR-II antiserum. TβR-I/JD1(Δ150-181), like the wild-type TβR-I, was able to bind TGF-β in a $Zn^{2+}$-inducible manner and form a physiological complex with TBR-II.

The signalling activities of TβR-I/JD1(Δ150-181) were determined by testing its ability to rescue biological responses to TGF-β in R4-2 cells. The induction of PAI-1 and fibronectin were examined since these responses in the parent Mv1Lu cells are well-characterized and are representative of the various matrix proteins induced by TGF-β. In Mv1Lu cells, synthesis of PAI-1 was increased by the treatment with TGF-β, but not in R4-2 cells transfected with the vector alone. When R4-2 cells were transfected with the wild-type TβR-I or TβR-I/JD1(Δ150-181), the cells produced PAI-1 upon treatment with TGF-β in the presence of $ZnCl_2$. Similarly, fibronectin production by TGF-β was restored in R4-2 cells transfected with the wild-type TβR-I and less potently in the cells transfected with TβR-I/JD1 (Δ150-181). PAI-1 and fibronectin production were not stimulated in the absence of $ZnCl_2$, indicating that the signals for the induction of PAI-1 and fibronectin were rescued by the exogenous receptors.

Figure 2:
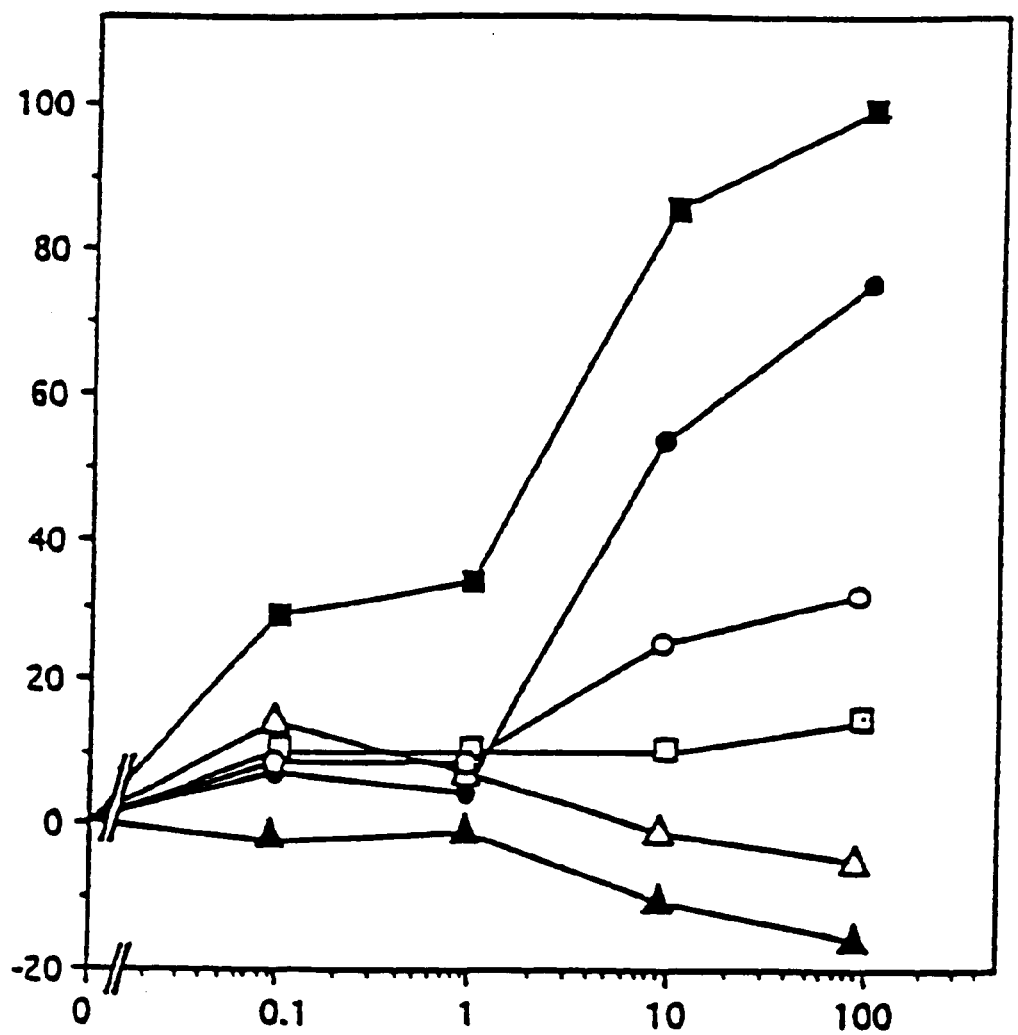
FIG. 2 shows the antiproliferative response in R4-2 cells transfected with wild-type TβR-I and mutant derivatives. The results are reported as % inhibition of [$^3$H]-thymidine incorporation against increasing concentrations (ng/ml) of TGF-βI.

To evaluate whether TβR-I/JD1(Δ150-181) is able to restore TGFβ antiproliferative effect, DNA synthesis assay was performed by measuring the incorporation of [$^3$H] thymidine into the DNA (FIG. 2). Upon treatment with TGF-β, [$^3$H]thymidine incorporation into the DNA of Mv1Lu cells was inhibited dose-dependently up to 97% (closed squares), whereas TGF-β had no effect on the [$^3$H]thymidine incorporation in the R4-2 cells transfected with the vector alone (open squares). When R4-2 cells transfected with the wild-type TβR-I were treated with TGF-β in the presence of ZnCl$_2$ (closed circles), [$^3$H] thymidine incorporation into the DNA was inhibited by 65–75%, whereas only a marginal inhibition was observed in the absence of ZnCl$_2$ (open circles). In contrast, R4-2 cells transfected with TβR-I/JD1(Δ150-181) were refractory to TGF-β growth inhibition in the presence or absence of ZnCl$_2$ (closed triangles, open triangles, respectively). These results suggested that the N-terminal half of the cytoplasmic juxtamembrane domain of TβR-I was not required for signalling extracellular matrix responses, whereas it was essential for signalling growth inhibitory activity.

The inability of TβR-I/JD1(Δ150-181) to mediate a growth inhibitory signal raised the possibility that the N-terminal half of the cytoplasmic juxtamembrane domain of TβR-I contains a site for interaction with downstream component which transduces a signal specific for growth inhibition. Alternatively, such a deletion might change the structural conformation, yielding a receptor which is unable to transduce signals even if the substrate interaction sites were preserved. To address these questions, missense mutations instead of deletion were introduced into certain serine and threonine residues in the TβR-I juxtamembrane region that was deleted in TβR-1/JD1(Δ150-181) . As an initial attempt, serine 165, serine 172 and threonine 176 were chosen since these serine and threonine residues were rather conserved among the type I receptors for the TGF-β superfamily, especially in ActR-IB, which transduces growth inhibition and PAI-1 signals by activin A. Ser and Thr residues were mutated simultaneously or individually to alanine and valine residues, respectively, resulting in four different expression constructs including TβR-I/JM123 (S165A/S172A/T176V), TβR-I/JM1(S165A), TβR-I/JM2 (S172A) and TβR-I/JM3 (T176V). These constructs were stably transfected into R4-2 cells, and their expression, TGF-β binding and physical association with TβR-II were examined by affinity cross-linking with $^{125}$I-TGF-β1 followed by immunoprecipitation using anti-TβR-II antiserum. All the different receptor mutants were expressed on the cell surface and bound TGF-β in complex with TβR-II in a Zn$^{2+}$-dependent manner.

Figure 3:
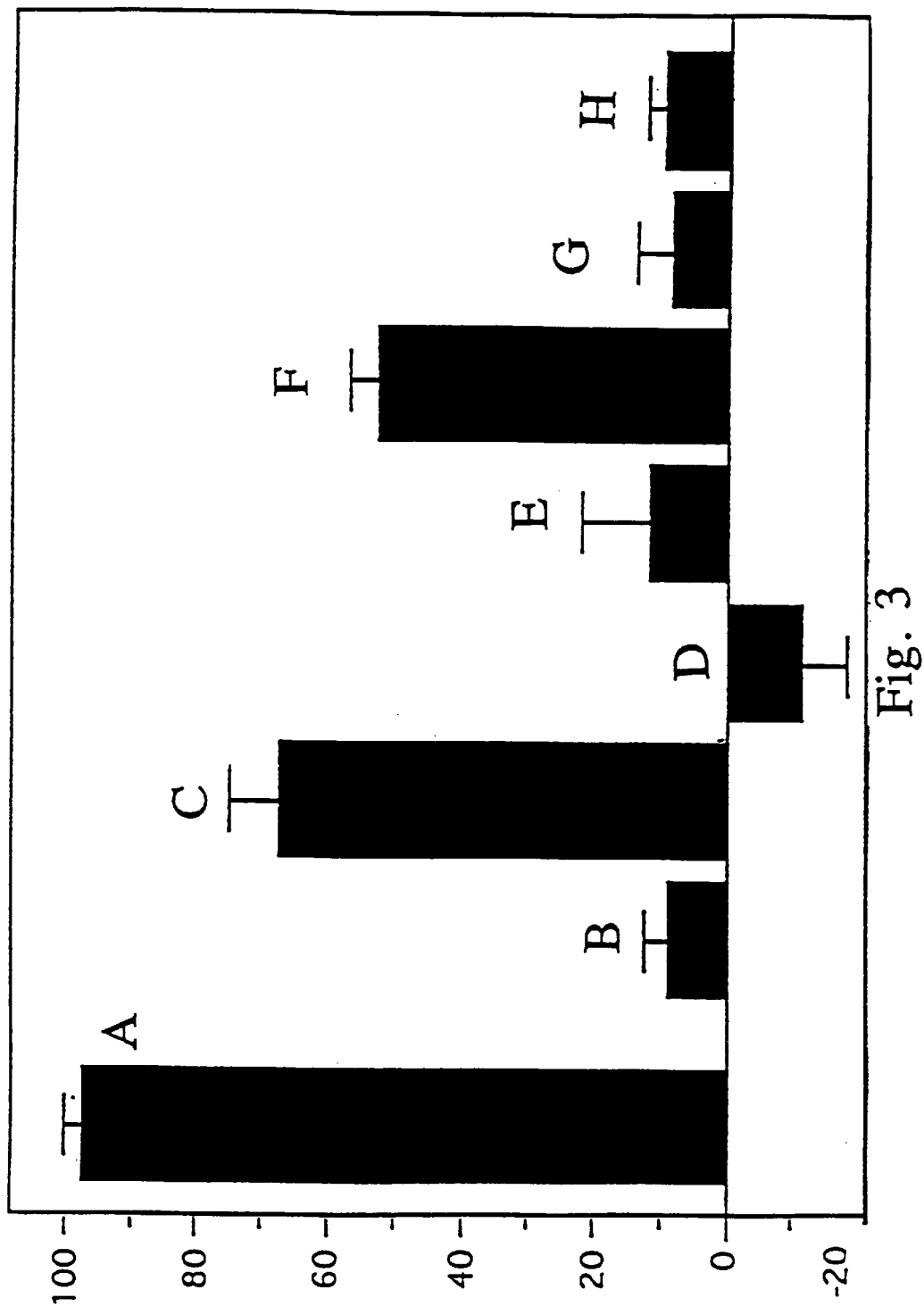
FIG. 3 shows the inhibition of [$^3$H]-thymidine incorporation in R4-2 cells expressing wild-type TβR-I and mutant derivatives.

To test the signalling activities of these missense mutant forms of TβR-I, the transfected cells were subjected to the analyses for extracellular matrix production and growth inhibition by TGFβ. In PAI-1 and fibronectin assays, like wild-type TβR-I and TβR-IND1(Δ150-181), all the constructs analyzed including TβR-I/JM123(S165A/S172A/ T176V), TβR-I/JM1(S165A), TβRI/JM2(S172A) and TβR-I/JM3(T176V) restored responsiveness to TGF-β. With regard to TGF-β antiproliferative effect, the TβR-I/JM1 (S165A) (FIG. 3F) construct mediated a growth inhibitory effect comparable to that mediated by the wild-type TβR-I (FIG. 3C), whereas TβR-I/JM123(S165A/S172A/T176V) (FIG. 3E), TβR-I/JM2(S172A) (FIG. 3G) and TβR-I/JM3 (T176V) (FIG. 3H) were unable to restore this activity. Columns A in FIG. 3 reports the results for Mv1Lu (no DNA transfected). The other columns report the results for R4-2 cells, B being for vector and D being for TβR-I/JD1(Δ150-181).

The difference among TβR-I and its mutant derivatives in their ability to restore responsiveness to TGF-β might be due to altered catalytic activity of their receptor kinase. To address this issue, kinase activity was determined by expressing the cytoplasmic regions of TβR-I and its mutants as GST fusion proteins in *E. coli* and testing their kinase activities in vitro. The protein products of wild-type TβR-I (GST-WT) and all the mutant constructs including GST-JD1 (Δ150-181), GST-JM123(S165A/S172A/T176V), GST-JM1 (S165A), GST-JM2(S172A) and GST-JM3(T176V) became phosphorylated to a similar extent. These observations indicate that all the mutant constructs of TβR-I used in these experiments were active as kinases at least in vitro.

We claim:

1. A nucleic acid molecule that encodes a mutant mammalian TGF-β type I receptor (TβR-I) polypeptide, wherein one or more amino acid residues in the cytoplasmic juxtamembrane region between the transmembrane and GS domains of the corresponding wild-type receptor are substituted with other amino acids or deleted, and wherein the mutant polypeptide substantially retains the ability of said corresponding wild-type mammalian TGF-β type I receptor to transduce a signal leading to matrix protein production but has substantially reduced ability relative to the corresponding wild-type mammalian receptor to mediate a growth-inhibitory signal.

2. The nucleic acid molecule according to claim 1, wherein the mutant receptor mediates a growth inhibitory signal no greater than 50% of that mediated by the corresponding wild-type receptor under the same conditions.

3. The nucleic acid molecule according to claim 1, wherein the mutant receptor mediates a growth inhibitory signal no greater than 25% of that mediated by the corresponding wild-type receptor under the same conditions.

4. The nucleic acid molecule according to claim 1, wherein said juxtamembrane region corresponds to amino acid residues 150–176 of human TβR-I.

5. The nucleic acid molecule according to claim 4, which comprises a missense mutation corresponding to an aminoacid residue selected from the group consisting of serine 172 and threonine 176.

6. The nucleic acid molecule according to claim 1, wherein the mutant receptor has the amino acid sequence of human TβR-I from which said juxtamembrane region has been deleted.

7. The nucleic acid molecule according to claim 6, wherein said juxtamembrane region consists of amino acid residues 150–176 of human TβR-I.

8. The nucleic acid molecule according to claim 1, wherein the mutant receptor has the amino acid sequence of human TβR-I in which serine 172 has been replaced by another amino acid residue.

9. The nucleic acid molecule according to claim 1, wherein the mutant receptor has the amino acid sequence of human TβR-I in which threonine 176 has been replaced by another amino acid residue.

10. A replicable expression vector comprising the nucleotide sequence of the nucleic acid molecule of any one of claims 1 to 9.

11. A prokaryotic cell line transformed with the replicable expression vector according to claim 10.

12. An eukaryotic cell line transfected with the replicable expression vector according to claim 10.

13. A method for the identification of substances having antiproliferative activity, comprising:

providing the eukaryotic cell line as claimed in claim 12, contacting the eukaryotic cell with a substance or a mixture of substances, and determining the proliferation of the eukaryotic cell relative to a control as a measure of the antiproliferative activity of the substance or mixture of substances.

14. A polypeptide comprising the amino acid sequence of a mutant mammalian TGF-β type I receptor (TβR-I) polypeptide, wherein one or more amino acid residues in the cytoplasmic juxtamembrane region between the transmembrane and GS domains of the corresponding wild-type receptor are substituted with other amino acids or deleted, and wherein the mutant polypeptide substantially retains the ability of said corresponding wild-type mammalian TGF-β type I receptor to transduce a signal leading to matrix protein production but has substantially reduced ability relative to the corresponding wild-type mammalian receptor to mediate a growth-inhibitory signal.

15. A complex of the polypeptide according to claim 14 and a type II receptor.

16. The polypeptide according to claim 14, comprising the substitution of an amino acid residue corresponding to serine 172 or threonine 176 of human TβR-I.

17. The polypeptide according to claim 14, wherein the mutant receptor has the amino acid sequence of human TβR-I from which said juxtamembrane region has been deleted.

18. The polypeptide according to claim 17, wherein said juxtamembrane region consists of amino acid residues 150–176 of human TβR-I.

19. The polypeptide according to claim 14, wherein the mutant receptor has the amino acid sequence of human TβR-I in which serine 172 has been replaced by another amino acid residue.

20. The polypeptide according to claim 14, wherein the mutant receptor has the amino acid sequence of human TβR-I in which threonine 176 has been replaced by another amino acid residue.

* * * * *

SEQUENCE LISTING

```
<160> NUMBER OF SEQ ID NOS: 19

<210> SEQ ID NO 1
<211> LENGTH: 24
<212> TYPE: DNA
<213> ORGANISM: Homo sapiens

<400> SEQUENCE: 1 gtcccgggctg ccacaaccgc act                                    24

<210> SEQ ID NO 2
<211> LENGTH: 21
<212> TYPE: DNA
<213> ORGANISM: Homo sapiens

<400> SEQUENCE: 2
gccccgggtt atgatatgac a                                       21

<210> SEQ ID NO 3
<211> LENGTH: 21
```

```
<212> TYPE: DNA
<213> ORGANISM: Homo sapiens

<400> SEQUENCE: 3
ggaagcttga ccatggaggc g                                              21

<210> SEQ ID NO 4
<211> LENGTH: 25
<212> TYPE: DNA
<213> ORGANISM: Homo sapiens

<400> SEQUENCE: 4
aggcggccgc ttacattttga tgcc                                          25

<210> SEQ ID NO 5
<211> LENGTH: 22
<212> TYPE: DNA
<213> ORGANISM: Homo sapiens

<400> SEQUENCE: 5
gtggcagata tagaccatca ac                                             22

<210> SEQ ID NO 6
<211> LENGTH: 25
<212> TYPE: DNA
<213> ORGANISM: Homo sapiens

<400> SEQUENCE: 6
ctatatctgc cactatgata tgaca                                          25

<210> SEQ ID NO 7
<211> LENGTH: 23
<212> TYPE: DNA
<213> ORGANISM: Homo sapiens

<400> SEQUENCE: 7
cctgcattag atcgcccttt tat                                            23

<210> SEQ ID NO 8
<211> LENGTH: 24
<212> TYPE: DNA
<213> ORGANISM: Homo sapiens

<400> SEQUENCE: 8
cgccctttta ttgcagaggg tact                                           24

<210> SEQ ID NO 9
<211> LENGTH: 21
<212> TYPE: DNA
<213> ORGANISM: Homo sapiens

<400> SEQUENCE: 9
gagggtactg tgttgaaaga c                                              21

<210> SEQ ID NO 10
<211> LENGTH: 23
<212> TYPE: DNA
<213> ORGANISM: Homo sapiens

<400> SEQUENCE: 10 ataaagggc gatctaatgc agg                                             23

<210> SEQ ID NO 11
```

```
<211> LENGTH: 24
<212> TYPE: DNA
<213> ORGANISM: Homo sapiens

<400> SEQUENCE: 11
agtaccctct gcaataaaag ggcg                                              24

<210> SEQ ID NO 12
<211> LENGTH: 21
<212> TYPE: DNA
<213> ORGANISM: Homo sapiens

<400> SEQUENCE: 12
gtctttcaac acagtaccct c                                                 21

<210> SEQ ID NO 13
<211> LENGTH: 57
<212> TYPE: PRT
<213> ORGANISM: Homo sapiens

<400> SEQUENCE: 13
```

Asn Arg Thr Val Ile His His Arg Val Pro Asn Glu Glu Asp Pro Ser
1               5                   10                  15

Leu Asp Arg Pro Phe Ile Ser Glu Gly Thr Thr Leu Lys Asp Leu Ile
            20                  25                  30

Tyr Asp Met Thr Thr Ser Gly Ser Gly Ser Gly Leu Pro Leu Leu Val
        35                  40                  45

Gln Arg Thr Ile Ala Arg Thr Ile Val
    50                  55

```
<210> SEQ ID NO 14
<211> LENGTH: 60
<212> TYPE: PRT
<213> ORGANISM: Homo sapiens

<400> SEQUENCE: 14
```

Lys Arg Arg Asn Gln Glu Arg Leu Asn Pro Arg Asp Val Glu Tyr Gly
1               5                   10                  15

Thr Ile Glu Gly Leu Ile Thr Thr Asn Val Gly Asp Ser Arg Leu Ala
            20                  25                  30

Asp Leu Leu Asp His Ser Cys Thr Ser Gly Ser Gly Ser Gly Leu Pro
        35                  40                  45

Phe Leu Val Gln Arg Thr Val Ala Arg Gln Ile Thr
    50                  55                  60

```
<210> SEQ ID NO 15
<211> LENGTH: 56
<212> TYPE: PRT
<213> ORGANISM: Homo sapiens

<400> SEQUENCE: 15
```

Gln Arg Val Tyr His Asn Arg Gln Arg Leu Asp Met Glu Asp Pro Ser
1               5                   10                  15

Cys Glu Met Cys Leu Ser Lys Asp Lys Thr Leu Gln Asp Leu Val Tyr
            20                  25                  30

Asp Leu Ser Thr Ser Gly Ser Gly Ser Gly Leu Pro Leu Phe Val Gln
        35                  40                  45

Arg Thr Val Ala Arg Thr Ile Val
    50                  55

```
<210> SEQ ID NO 16
<211> LENGTH: 56
<212> TYPE: PRT
<213> ORGANISM: Homo sapiens

<400> SEQUENCE: 16

Cys Lys Ser Ile Ser Ser Arg Arg Arg Tyr Asn Arg Asp Leu Glu Gln
1               5                   10                  15

Asp Glu Ala Phe Ile Pro Val Gly Glu Ser Leu Lys Asp Leu Ile Asp
            20                  25                  30

Gln Ser Gln Ser Ser Gly Ser Gly Ser Gly Leu Pro Leu Leu Val Gln
        35                  40                  45

Arg Thr Ile Ala Lys Gln Ile Gln
    50                  55

<210> SEQ ID NO 17
<211> LENGTH: 55
<212> TYPE: PRT
<213> ORGANISM: Homo sapiens

<400> SEQUENCE: 17

Lys Arg Gln Glu Ala Arg Pro Arg Tyr Ser Ile Gly Leu Glu Gln Asp
1               5                   10                  15

Glu Thr Tyr Ile Pro Pro Gly Glu Ser Leu Arg Asp Leu Ile Glu Gln
            20                  25                  30

Ser Gln Ser Ser Gly Ser Gly Ser Gly Leu Pro Leu Leu Val Gln Arg
        35                  40                  45

Thr Ile Ala Leu Gln Ile Gln
    50                  55

<210> SEQ ID NO 18
<211> LENGTH: 60
<212> TYPE: PRT
<213> ORGANISM: Homo sapiens

<400> SEQUENCE: 18

Arg Arg Arg Gln Glu Lys Gln Arg Gly Leu His Ser Glu Leu Gly Glu
1               5                   10                  15

Ser Ser Leu Ile Leu Lys Ala Ser Glu Gln Gly Asp Thr Met Leu Gly
            20                  25                  30

Asp Leu Leu Asp Ser Asp Cys Thr Thr Gly Ser Gly Ser Gly Leu Pro
        35                  40                  45

Phe Leu Val Gln Arg Thr Val Ala Arg Gln Val Ala
    50                  55                  60

<210> SEQ ID NO 19
<211> LENGTH: 8
<212> TYPE: PRT
<213> ORGANISM: Homo sapiens

<400> SEQUENCE: 19

Thr Thr Ser Gly Ser Gly Ser Gly
1               5
```